United States Patent
Kim et al.

(10) Patent No.: US 7,641,904 B2
(45) Date of Patent: Jan. 5, 2010

(54) IL-32 MONOCLONAL ANTIBODIES AND USES THEREOF

(75) Inventors: Ki-Hong Kim, Changwon-si (KR); Jung-Hyun Shim, Daejeon (KR); Min-chul Cho, Seoul (KR); Jung-Woo Kang, Daejeon (KR); Hee-Sook Choi, Gwangmyeong-si (KR); Eun-Hee Seo, Pohang-si (KR); Eun-young Song, Seoul (KR); Hee-Gu Lee, Daejeon (KR); Mi-Young Park, Daejeon (KR); Do-Young Yoon, Seoul (KR)

(73) Assignee: Konkuk University Industrial Cooperation Corp., Seoul (KR)

( * ) Notice: Subject to any disclaimer, the term of this patent is extended or adjusted under 35 U.S.C. 154(b) by 0 days.

(21) Appl. No.: 12/032,298

(22) Filed: Feb. 15, 2008

(65) Prior Publication Data

US 2008/0219995 A1    Sep. 11, 2008

Related U.S. Application Data

(60) Provisional application No. 60/938,392, filed on May 16, 2007.

(30) Foreign Application Priority Data

Feb. 16, 2007    (KR) .................. 10-2007-0016477

(51) Int. Cl.
    *A61K 39/395*    (2006.01)
    *C12P 21/08*    (2006.01)
(52) U.S. Cl. ............. 424/141.1; 530/388.1; 530/809; 530/351; 530/391.3; 530/391.7; 424/178.1; 435/7.92; 435/188; 435/975; 435/70.21
(58) Field of Classification Search ........... None
    See application file for complete search history.

(56) References Cited

U.S. PATENT DOCUMENTS

| | | | |
|---|---|---|---|
| 3,817,837 A | 6/1974 | Rubenstein et al. | 195/103.5 |
| 3,850,752 A | 11/1974 | Schuurs et al. | 195/103.5 |
| 3,939,350 A | 2/1976 | Kronick et al. | 250/365 |
| 3,996,345 A | 12/1976 | Ullman et al. | 424/12 |
| 4,275,149 A | 6/1981 | Litman et al. | 435/7 |
| 4,277,437 A | 7/1981 | Maggio | 422/61 |
| 4,366,241 A | 12/1982 | Tom et al. | 435/7 |
| 4,472,509 A | 9/1984 | Gansow et al. | 436/548 |
| 4,938,948 A | 7/1990 | Ring et al. | 424/9 |
| 5,021,236 A | 6/1991 | Gries et al. | 424/9 |
| 5,196,066 A | 3/1993 | Kusuda et al. | 118/612 |
| 2007/0071719 A1* | 3/2007 | Kim et al. | 424/85.2 |

FOREIGN PATENT DOCUMENTS

WO    WO 2005/047478    5/2005

OTHER PUBLICATIONS

Asquith and McInnes, "Emerging cytokine targets in rheumatoid arthritis," *Curr. Opin. Rheumatol.*, 19(3):246-251, 2007.
Brennan and Beech, "Update on cytokines in rheumatoid arthritis," *Curr. Opin. Rheumatol.*, 19(3):296-301, 2007.
Cagnard et al., "Interleukin-32, CCL2, PF4F1 and GFD10 are the only cytokine/chemokine genes differentially expressed by in vitro cultured rheumatoid and osteoarthritis fibroblast-like synoviocytes," *Eur. Cytokine Netw.*, 16(4):289-292, 2005.
Chen et al., "The newest interleukins: recent additions to the ever-growing cytokine family," *Vitam. Horm.*, 74:207-228, 2006.
Conti et al., "Modulation of autoimmunity by the latest interleukins (with special emphasis on IL-32," *Autoimmun. Rev.*, 6(3):131-137, 2007.
Dinarello and Kim, "IL-32, a novel cytokine with a possible role in disease," *Ann. Rheum. Dis.*, 65(3):iii61-64, 2006.
Goda et al., "Involvement of IL-32 in activation-induced cell death in T cells," *International Immunology*, 18(2):233-240, 2006.
Joosten et al., "IL-32, a proinflammatory cytokine in rheumatoid arthritis, " *Proc. Natl. Acad. Sci. USA*, 103(9):3298-3303, 2006.
Kim et al., "Interleukin-32: a cytokine and inducer of TNFalpha," *Immunity*, 22(1):131-142, 2005.
Kim et al., "Interleukin-32 monoclonal antibodies for immunohistochemistry, Western blotting, and ELISA," *Journal of Immunological Methods*, 333:38-50, 2008.
Kundu and Basu, "IL-32: an emerging player in the immune response network against tuberculosis?," *PLoS Med.*, 3(8):e274, 2006.
Netea et al., "IL-32 synergizes with nucleotide oligomerization domain (NOD) 1 and NOD2 ligands for IL-1beta and IL-6 production through a caspase 1-dependent mechanism," *PNAS*, 102(45):16309-16314, 2005.
Netea et al., "Mycobacterium tuberculosis induces interleukin-32 production through a caspase-1/IL-18/interferon-gamma-dependent mechanism," *PLoS Med.*, 3(8):e277, 2006.
Novick et al., "Proteinase 3 is an IL-32 binding protein," *PNAS*, 103(9):3316-3321, 2006.
Shoda et al., "Interactions between IL-32 and tumor necrosis factor alpha contribute to the exacerbation of immune-inflammatory diseases," *Arthritis Research & Therapy*, 8(6):R166, 2006.

* cited by examiner

*Primary Examiner*—Dong Jiang
(74) *Attorney, Agent, or Firm*—Fulbright & Jaworski L.L.P.

(57) ABSTRACT

The present invention provides monoclonal antibodies specific for interleukin-32 (IL-32, previously referred to as "natural killer cell transcript 4" or "NK4") and hybridomas secreting monoclonal antibodies specific for IL-32. Also provided are diagnostic methods and kits (e.g., ELISA, Western blot, etc.) which utilize monoclonal antibodies specific for IL-32.

15 Claims, 7 Drawing Sheets

IL-32 MONOCLONAL ANTIBODIES AND USES THEREOF

CROSS-REFERENCE TO RELATED APPLICATIONS

This application claims the benefit of U.S. Provisional patent application 60/938,392, filed May 16, 2007, which claims priority to Korean Patent Application No. 10-2007-16477 filed on Feb. 16, 2007, the entire disclosures of which are specifically incorporated herein by reference in their entirety without disclaimer.

BACKGROUND OF THE INVENTION

1. Field of the Invention

The present invention relates generally to the fields of molecular biology, immunobiology, and medicine. More particularly, it concerns monoclonal antibodies which specifically bind interleukin-32 (IL-32), and uses thereof.

2. Description of Related Art

Cytokine IL-32 is a recently discovered proinflammatory cytokine. IL-32 has four isoforms ($\alpha$, $\beta$, $\gamma$, $\delta$) which all lack sequence homology with previously identified cytokine families (Kim et al., 2005). IL-32 induces IL-1$\beta$, TNF-$\alpha$, IL-6, and chemokines, and IL-32 is an IL-18 inducible gene (Joosten et al., 2006; Kim et al. 2005).

IL-32 has been implicated in several disease states, including inflammatory diseases such as arthritis (Breenan and Beech, 2007; Asquith and McInnes, 2007), Crohn's disease, and autoimmune or immune-inflammatory diseases (Conti et al., 2007; Dinarello and Kim, 2006). IL-32 may also play a role in immune responses to tuberculosis (Kundu and Basu, 2006; Netea et al., 2006).

Presently, limited tools exist for the evaluation of IL-32. Although an anti-IL-32 polyclonal antibody is commercially available, monoclonal antibodies directed towards the isoforms of IL-32 have not yet been developed. Clearly, there is a need for additional tools for the evaluation and manipulation of IL-32.

SUMMARY OF THE INVENTION

The present invention overcomes limitations in the prior art by providing monoclonal antibodies directed towards IL-32. Certain monoclonal antibodies of the present invention selectively bind a single the IL-32 isoform; for example, the KU32-07 monoclonal antibody selectively recognizes only the IL-32$\alpha$ isoform. Other monoclonal antibodies of the present invention selectively recognize multiple IL-32 isoforms; for example, the KU32-52 monoclonal antibody selectively binds the IL-32$\alpha$, IL-32$\beta$, and IL-32$\gamma$ isoforms. The present invention also provides kits and methods for the use of anti-IL-32 monoclonal antibodies.

The present invention also provides the identification of various antigenic regions in IL-32$\alpha$ and IL-32$\beta$ which may be bound, in certain embodiments, by a monoclonal antibody of the present invention. In various embodiments, an anti-IL-32 monoclonal antibody may bind amino acids 91-131 of IL-32$\alpha$ or amino acids 71-107 of IL-32$\beta$.

An aspect of the present invention relates to a monoclonal antibody which selectively binds an interleukin-32 (IL-32) protein. The antibody may selectively bind IL-32$\alpha$. In certain embodiments, the antibody recognizes or binds amino acids 91 to 131 of IL-32$\alpha$. The antibody may be the KU32-07 antibody. The antibody may selectively bind IL-32$\alpha$, IL-32$\beta$, and IL-32$\beta$. In certain embodiments, the antibody recognizes or binds amino acids 71 to 107 of IL-32$\beta$. The antibody may be the KU32-52 antibody. The antibody may be a IgG, IgM, IgA, IgD or IgE. In certain embodiments, the antibody is an IgG, such as an IgG1 or IgG2.

The antibody may be labeled with an agent, such as a diagnostic agent. The diagnostic agent may be a magnetic spin resonance label, a fluorescent label, a radiolabel, a chemiluminescent label, a fluorochrome, or an enzyme. The agent may be a therapeutic agent. The therapeutic agent may be a radioisotope, a chemotherapeutic, a toxin, a cytokine or an enzyme. The antibody may be humanized. The antibody may be comprised in a pharmaceutical preparation.

Another aspect of the present invention relates to a hybridoma cell producing a monoclonal antibody of the present invention. In certain embodiments, the hybridoma cell is KCLRF-BP-00149 or KCLRF-BP-00150.

Yet another aspect of the present invention relates to a method for determining the concentration of a IL-32 protein in a sample, wherein the sample contains or is suspected of containing a IL-32 protein, and wherein the method comprises contacting the sample with the monoclonal antibody of the present invention. The method may further comprise contacting the sample with a polyclonal antibody, wherein the polyclonal antibody specifically binds the IL-32 protein. The polyclonal antibody may be bound to or associated with a plate or solid support. The method may comprise a sandwich ELISA test. The monoclonal antibody may be the KU32-07 antibody. The test may be a radioimmunoassay (RIA), immunoradiometric assay, fluoroimmunoassay, chemiluminescent assay, bioluminescent assay, or a Western blot. The sample may comprise a blood sample, a serum sample, a tissue sample, a urine sample, a or a cerebrospinal fluid sample. The sample may be obtained from a human. The method may further comprise a method of diagnosing the presence or the progression of a disease, such as an inflammatory disease. The inflammatory disease may be Crohn's disease, colitis, rheumatoid arthritis, osteoarthritis, psoriasis, or cancer.

Another aspect of the present invention relates to a method of treating an inflammatory disease comprising administering to a subject the monoclonal antibody of the present invention. The antibody may be the KU32-07 antibody or the KU32-52 antibody. The subject may be a mammal, such as a mouse, a rat, or a human.

Yet another aspect of the present invention relates to a kit comprising a monoclonal antibody of the present invention in a suitable container means. The kit may further comprise a polyclonal antibody specific for said IL-32 protein in a second container means. The kit may comprise an ELISA test to measure the presence, absence, or amount of said IL-32 protein. The kit may comprise a monoclonal antibody which selectively recognizes IL-32$\alpha$. The monoclonal antibody may be KU32-07. The kit may comprise an radioimmunoassay (RIA), immunoradiometric assay, fluoroimmunoassay, chemiluminescent assay, bioluminescent assay, or Western blot to measure the presence, absence, or amount of said IL-32 protein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
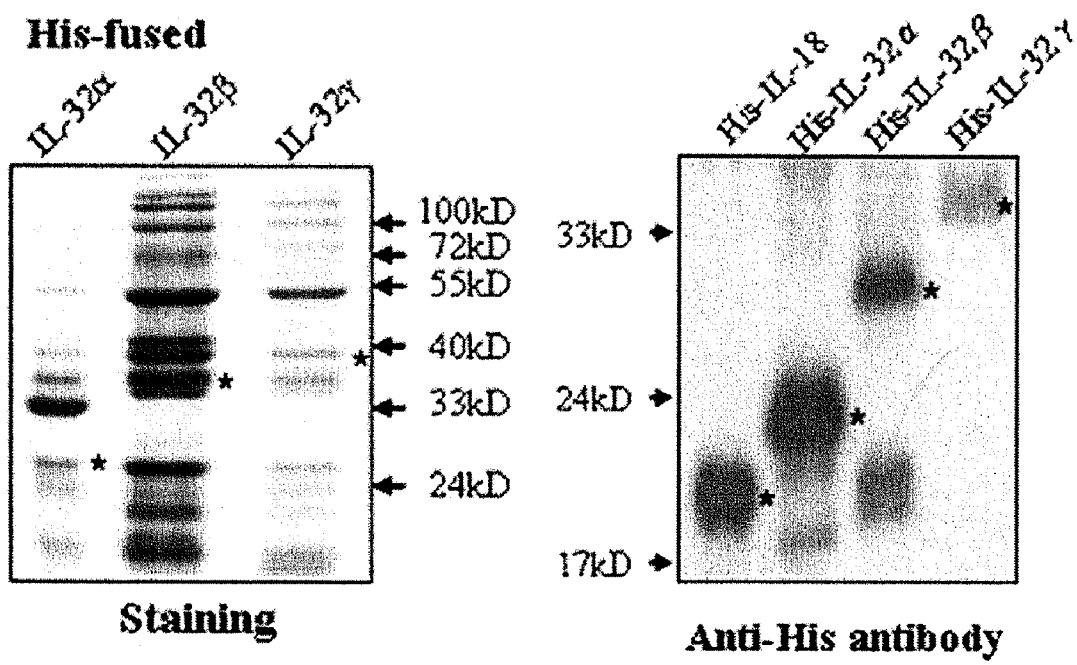
FIG. 1: 12% SDS-PAGE and Western blotting of His-IL-32α, β, γ recombinant proteins.

The present invention provides monoclonal antibodies directed towards one or more isoforms of IL-32. Certain monoclonal antibodies of the present invention selectively bind a single the IL-32 isoform; for example, the KU32-07 monoclonal antibody selectively recognizes only the IL-32α isoform. Other monoclonal antibodies of the present invention selectively recognize multiple IL-32 isoforms; for example, the KU32-52 monoclonal antibody selectively binds the IL-32α, IL-32β, and IL-32γ isoforms. The present invention also provides hybridomas which secret IL-32 specific monoclonal antibodies, kits comprising monoclonal anti-IL-32 antibodies, diagnostic systems and methods using IL-32 specific monoclonal antibodies.

I. Evaluation of Disease States Using Anti-IL-32 Monoclonal Antibodies

Monoclonal antibodies specific for one or more IL-32 isoform may be used to detect, diagnose and/or treat a disease state. The presence, absence, or concentration of IL-32 in a biological sample may be evaluated using monoclonal antibodies of the present invention. For example, a tissue sample, serum sample, blood sample, urine sample, fecal sample, cerebrospinal fluid "CSF" sample, and/or a tissue sample may be obtained from a subject, such as a human patient. The sample may then be analyzed immunologically, e.g., via an ELISA, Western blot, etc. using an antibody of the present invention. It is anticipated that any disease associated with altered IL-32 expression may be evaluated, e.g., used to help diagnose, using antibodies of the present invention.

A. Inflammatory Diseases

Certain inflammatory diseases may be evaluated or diagnosed using monoclonal antibodies of the present invention to detect or quantify IL-32 levels. In certain embodiments, an increase or decrease in IL-32 levels, relative to a control sample or a normal individual, may be used to assess the presence or progression of a disease such as an inflammatory disease.

Additionally, evaluation of IL-32 may also be used to provide helpful insights regarding other cytokines and cellular factors involved in a disease state. For example, IL-32 induces production of tumor necrosis factor, macrophage inflammatory protein (MIP)-2 and IL-8 in monocytic cell lines. Additionally, IL-32 may be upregulated in activated T cells and NK cells, with IL-32β being predominantly expressed in activated T cells (Goda et al., 2006). IL-32 activates typical cytokine signal pathways of nuclear factor-kappa B (NF-κB) and p38 mitogen-activated protein kinase (Kim et al., 2005).

Disease states which may be evaluated or diagnosed using monoclonal antibodies of the present invention include Crohn's disease, psoriasis, psoriatic arthritis, rheumatoid arthritis, juvenile rheumatoid arthritis, osteoarthritis, tuberculosis infection, ankylosing spondylitis, enteropathic arthritis, reactive arthritis, undifferentiated spondyloarthropathy, juvenile spondyloarthropathy, Behcet's disease, enthesitis, ulcerative colitis, irritable bowel syndrome, inflammatory bowel disease, fibromyalgia, chronic fatigue syndrome, pain conditions associated with systemic inflammatory disease, systemic lupus erythematosus, Sjogren's syndrome, juvenile onset diabetes mellitus (also known as Type I diabetes mellitus), Wegener's granulomatosis, polymyositis, dermatomyositis, inclusion body myositis, multiple endocrine failure, Schmidt's syndrome, autoimmune uveitis, Addison's disease, Graves Disease, Hashimoto's thyroiditis, autoimmune thyroid disease, pernicious anemia, gastric atrophy, chronic hepatitis, lupoid hepatitis, atherosclerosis, presenile dementia, Alzheimer's disease, demyelating diseases, multiple sclerosis, amyotrophic lateral sclerosis, hypoparathyroidism, Dressler's syndrome, myasthenia gravis, Eaton-Lambert syndrome, autoimmune thrombocytopenia, idiopathic thrombocytopenic purpura, hemolytic anemia, pemphigus vulgaris, pemphigus, dermatitis herpetiformis, alopecia, scleroderma, progressive systemic sclerosis, CREST syndrome (calcinosis, Raynaud's phenomenon, esophageal dysmotility, sclerodactyl), and telangtasia), adult onset diabetes mellitus (also known as Type II diabetes mellitus), mixed connective tissue disease, polyarteritis nodosa, systemic necrotizing vasculitis, glomerulonephritis, atopic dermatitis, atopic rhinitis, Goodpasture's syndrome, Chagas' disease, sarcoidosis, rheumatic fever, asthma, anti-phospholipidsyndrome, erythema multiform, Cushing's syndrome, autoimmune chronic active hepatitis, allergic disease, allergic encephalomyelitis, transfusion reaction, leprosy, malaria, leshmaniasis, trypanosomiasis, Takayasu's arteritis, polymyalgia rheumatica, temporal arteritis, shistosomiasis, giant cell arteritis, eczema, lymphomatoid granulomatosis, Kawasaki's disease, dengue fever, encephalomyelitis, endocarditis, endomyocardial fibrosis, endophthalmitis, erythroblastosis fetalis, eosinophilic faciitis, Shulman's syndrome, Felty's syndrome, Fuch's cyclitis, IgA nephropathy, Henoch-Schonlein purpura, graft versus host disease, transplantation rejection, human immunodeficiency virus infection, Epstein-Barr virus infection, mumps, echovirus infection, cardiomyopathy, parvovirus infection, rubella virus infection, anthrax infection, small pox infection, hepatitic C viral infection, tularemia, sepsis, periodic fever syndromes, pyogenic arthritis, Familial Mediterranean Fever, TNF-receptor associated periodic syndrome (TRAPS), Muckle-Wells syndrome, hyper-IgD syndrome, familial cold urticaria, Hodgkin's and Non-Hodgkin's lymphoma, renal cell carcinoma, or multiple myeloma. It is also envisioned that a therapeutic effect (e.g., decrease in inflammatory symptoms) may be achieved by administration of an antibody of the present invention to a subject, such as a human patient.

B. Cancer

IL-32 may also play a role in the development or suppression of various cancers. IL-32 is known to induce TNF-$\alpha$ (Kim et al., 2005). TNF-$\alpha$ (tumor necrosis factor) is secreted by activated monocytes or macrophages and has the property of inducing tumor necrosis. In other experiments, The human lung carcinoma cell line A549, which expresses only the IL-18R $\alpha$ chain, was transfected with IL-18R $\beta$ chain gene. When the transfected A549 cell line is treated with IL-18, IL-32 is expressed in response to IL-18 (Kim et al., 2005). Thus, modulation of IL-32 by antibodies of the present invention may be useful for evaluation, testing, and therapeutics related to various cancers.

It is also envisioned that antibodies of the present invention may be used in various embodiments as immunotherapeutics. For example, administration of a monoclonal anti-IL-32 antibody of the present invention to a patient undergoing chemotherapy may be used to decrease an inflammatory response of the patient. This approach may allow alleviation of side-effects associated with various cancer therapies, thus improving the quality of life for the patient and increasing the probability of a positive clinical outcome.

II. Monoclonal Anti-(IL-32) Antibodies

Monoclonal antibodies which specifically recognize one or more isoform of IL-32 may be generated via various methods. Techniques employing anti-IL-32 monoclonal antibodies (e.g., as therapeutic administration of the antibody to a subject, immunodetection methods such as ELISA assays, etc.) are also disclosed.

A. Definitions

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting. The term "antigen" is used herein to refer to a substance that is capable of interacting with the antibody and in the context of the present invention is meant to be a IL-32 protein, such as IL-32$\alpha$, IL-32$\beta$, or IL-32$\gamma$.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, 1988; incorporated herein by reference).

The term "immunoglobulin" is used herein to refer to a protein consisting of one or more polypeptides substantially encoded by an immunoglobulin gene. The recognized immunoglobulin genes include the $\kappa$, $\lambda$, $\alpha$, $\gamma$ (IgG1, IgG2, IgG3, IgG4), $\sigma$, $\epsilon$ and $\mu$ constant region genes and in nature multiple immunoglobulin variable region genes. One natural form of immunoglobulin is a tetramer comprising two identical pairs in which each pair has one light chain and one heavy chain. In each pair the heavy and light chain variable regions together provide the binding surface capable of interacting with the antigen. The term Vh is used herein to refer to the heavy chain variable region, and the term Vk is used herein to refer to the light chain variable region and in this instance in common with numerous monoclonal antibodies the light chain is a "kappa" (k) type chain.

However, "humanized" antibodies are also contemplated, as are chimeric antibodies from mouse, rat, or other species, bearing human constant and/or variable region domains, bispecific antibodies, recombinant and engineered antibodies and fragments thereof. Methods for the development of antibodies that are "custom-tailored" to the patient's dental disease are likewise known and such custom-tailored antibodies are also contemplated.

B. Generation of Monoclonal Antibodies

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

The methods for generating monoclonal antibodies (MAbs) generally begin using similar methods as those for preparing polyclonal antibodies. Typically, an antibody is prepared by immunizing an animal with an antigenic composition comprising part or all of an IL-32 protein and collecting antisera from that immunized animal.

For example, an immunized mouse needed for cell fusion can be obtained by primary injection with His-IL-32$\alpha$, $\beta$, $\gamma$ emulsified in TiterMax Gold (Research Adjuvant) and secondary booster injection 28 days after primary injection. Splenocytes acquired from the immunized mouse and NS-1 myeloma cell may be mixed in 7~10:1 ratios and polyethylene glycol may be added to fuse the cells. In order to select the fused cells, cell mixtures may be cultured in HAT (hypoxanthine aminopterin thymidine) media. When fused cells grow continually in HAT media, the cells may be transferred to HT media for cell proliferation. Cells specifically reacting with GST-IL-32 recombinant protein may be selected by ELISA (enzyme linked immunosorbent assay). By limiting dilution, a cell line which proliferates from one cell may be established.

Using the above approach, the present invention provides selected hybridoma clones designated KU32-07 and KU32-52 which were deposited under the provisions of the Budapest Treaty at the Korean Cell Line Research Foundation (Cancer Research Institute, Seoul National University College of Medicine, 28 Yongon-dong, Chonguo-Gu. Seoul, 110-744, Korea) on Jan. 11, 2007 (deposit No. KCLRF-BP-00149 and KCLRF-BP-00150, respectively). The isotype of the monoclonal antibody secreted by KU32-07 is IgG2b and that of KU32-52 is IgG1.

Monoclonal antibodies can be purified from ascites of mouse intra-peritoneally injected with the above hybridomas. By Western blotting, it may be confirmed that monoclonal antibodies are secreted by the hybridomas have high specificity to human IL-32.

For screening purposes, IL-32α, β, γ may be generated via various methods. IL-32α, β, γ genes may be amplified by RT-PCR (reverse transcriptase-polymerase chain reaction) and then cloned to *Escherichia coli* expression vector for production of one or more of the recombinant proteins. Recombinant proteins (His-fused IL-32α, β, γ and GST-fused IL-32α, β, γ) may be amplified by *E. coli* expression system and purified with Talon bead and Glutathion 4B sepharose beads. These proteins may then be used as antigens and for optimization of diagnostic kits.

A wide range of animal species can be used for the production of antisera. Typically the animal used for production of antisera is a rabbit, a mouse, a rat, a hamster, a guinea pig or a goat. The choice of animal may be decided upon the ease of manipulation, costs or the desired amount of sera, as would be known to one of skill in the art.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, chemokines, cofactors, toxins, plasmodia, synthetic compositions or LEEs or CEEs encoding such adjuvants.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m$^2$) (Johnson/Mead, NJ), cytokines such as γ-interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen including but not limited to subcutaneous, intramuscular, intradermal, intraepidermal, intravenous and intraperitoneal. The production of polyclonal antibodies may be monitored by sampling blood of the immunized animal at various points following immunization.

A second, booster dose (e.g., provided in an injection), may also be given. The process of boosting and titering is repeated until a suitable titer is achieved. When a desired level of immunogenicity is obtained, the immunized animal can be bled and the serum isolated and stored, and/or the animal can be used to generate MAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986), but mice are preferred, such as BALB/c mice which are routinely used and typically produce a high percentage of stable fusions.

The animals are injected with an IL-32 antigen, generally as described above. The antigen may be mixed with adjuvant, such as Freund's complete or incomplete adjuvant. Booster administrations with the same antigen or DNA encoding the antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. First, a sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. Second, the individual cell lines could be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is also contemplated that a molecular cloning approach may be used to generate monoclonals. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies. In another example, LEEs or CEEs can be used to produce antigens in vitro with a cell free system. These can be used as targets for scanning single chain antibody libraries. This would enable many different antibodies to be identified very quickly without the use of animals.

Alternatively, monoclonal antibody fragments encompassed by the present invention can be synthesized using an automated peptide synthesizer, or by expression of full-length gene or of gene fragments in E. coli.

C. Antibody Conjugates

The present invention further provides antibodies to IL-32 transcribed messages and translated proteins, polypeptides and peptides, generally of the monoclonal type, that are linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radio-labeled nucleotides, antiviral agents, chelating agents, cytokines, growth factors, and oligo- or poly-nucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Any antibody of sufficient selectivity, specificity or affinity may be employed as the basis for an antibody conjugate. Such properties may be evaluated using conventional immunological screening methodology known to those of skill in the art. Sites for binding to biological active molecules in the antibody molecule, in addition to the canonical antigen binding sites, include sites that reside in the variable domain that can bind pathogens, B-cell superantigens, the T cell co-receptor CD4 and the HIV-1 envelope (Sasso et al., 1989; Shorki et al., 1991; Silvermann et al., 1995; Cleary et al., 1994; Lenert et al., 1990; Berberian et al., 1993; Kreier et al., 1991). In addition, the variable domain is involved in antibody self-binding (Kang et al., 1988), and contains epitopes (idiotypes) recognized by anti-antibodies (Kohler et al., 1989).

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. Another such example is the formation of a conjugate comprising an antibody linked to a cytotoxic or anti-cellular agent, and may be termed "immunotoxins".

Antibody conjugates are generally preferred for use as diagnostic agents. Antibody diagnostics generally fall within two classes, those for use in in vitro diagnostics, such as in a variety of immunoassays, and/or those for use in vivo diagnostic protocols, generally known as "antibody-directed imaging".

Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions, radioactive isotopes, fluorochromes, NMR-detectable substances, or X-ray imaging compounds.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99}$ . . . by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetraacetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

III. Immunodetection Methods Using Monoclonal IL-32 Antibodies

In still further embodiments, monoclonal anti-IL-32 antibodies may be used in immunodetection methods for binding, purifying, removing, quantifying and/or otherwise generally detecting an IL-32 protein (e.g., selectively recognizing IL-32α). Immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev, 1999; Gulbis and Galand, 1993; De Jager et al., 1993; and Nakamura et al., 1987, each incorporated herein by reference.

The present invention provides certain specific methods and approaches for quantifying IL-32. Specifically, IL-32 protein can be measured quantitatively by coating a plate with a IL-32 polyclonal antibody, adding a sample containing or suspected of containing an IL-32 protein (e.g., IL-32α, β, γ recombinant protein) to the plate, and adding a monoclonal antibody of the present invention to the plate. Thus, a sandwich ELISA for quantification of IL-32 is provided by using a polyclonal antibody and a monoclonal antibody. This approach was confirmed in the below examples using IL-32α, β, γ recombinant proteins.

In general, the immunobinding methods include obtaining a sample suspected of containing IL-32 expressed message and/or protein, polypeptide and/or peptide, and contacting the sample with a first anti-IL-32 message and/or anti-IL-32 translated product antibody in accordance with the present invention, as the case may be, under conditions effective to allow the formation of immunocomplexes.

These methods include methods for purifying an IL-32 protein from an organelle, cell, tissue or organism's samples. In these instances, the antibody removes the antigenic IL-32 component from a sample. The antibody will preferably be linked to a solid support, such as in the form of a column matrix, and the sample suspected of containing the IL-32 message, protein, polypeptide and/or peptide antigenic component will be applied to the immobilized antibody. The unwanted components will be washed from the column, leaving the antigen immunocomplexed to the immobilized antibody to be eluted.

The immunobinding methods also include methods for detecting and quantifying the amount of an antigen component in a sample and the detection and quantification of any immune complexes formed during the binding process. Here, one would obtain a sample suspected of containing an antigen, and contact the sample with an antibody against the IL-32 antigen, and then detect and quantify the amount of immune complexes formed under the specific conditions.

In terms of antigen detection, the biological sample analyzed may be any sample that is suspected of containing an antigen, such as, for example, a tissue section or specimen, a homogenized tissue extract, a cell, an organelle, separated and/or purified forms of any of the above antigen-containing compositions, or even any biological fluid that comes into contact with the cell or tissue, including blood and/or serum, although tissue samples or extracts are preferred.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any IL-32 antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277, 437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The IL-32 antigen antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

The immunodetection methods of the present invention have evident utility in the diagnosis and prognosis of conditions such as various diseases wherein a specific or elevated IL-32 is expressed, such as arthritis etc. Here, a biological and/or clinical sample suspected of containing a specific disease associated IL-32 expression product is used. However, these embodiments also have applications to non-clinical samples, such as in the titering of antigen or antibody samples, for example in the selection of hybridomas.

In the clinical diagnosis and/or monitoring of patients with various forms a disease (e.g., arthritis or colitis), the detection of (e.g., elevated) expression of an IL-32 protein, may be determined and compared to the levels in a corresponding biological sample from a normal subject. However, as is known to those of skill in the art, such a clinical diagnosis would not necessarily be made on the basis of this method in isolation. Those of skill in the art are very familiar with differentiating between significant differences in types and/or amounts of biomarkers, which represent a positive identification, and/or low level and/or background changes of biomarkers. Indeed, background expression levels are often used to form a "cut-off" above which increased detection will be scored as significant and/or positive. Of course, the antibodies of the present invention in any immunodetection or therapy known to one of ordinary skill in the art.

A. ELISAs

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In one exemplary ELISA, the anti-IL-32 message and/or anti-IL-32 translated product antibodies are immobilized onto a selected surface exhibiting protein affinity, such as a well in a polystyrene microtiter plate. Then, a test composition suspected of containing the antigen, such as a clinical sample, is added to the wells. After binding and/or washing to remove non-specifically bound immune complexes, the bound antigen may be detected. Detection is generally achieved by the addition of another anti-IL-32 message and/or anti-IL-32 translated product antibody that is linked to a detectable label. This type of ELISA is a simple "sandwich ELISA". Detection may also be achieved by the addition of a second anti-IL-32 message and/or anti-IL-32 translated product antibody, followed by the addition of a third antibody that has binding affinity for the second antibody, with the third antibody being linked to a detectable label.

In another exemplary ELISA, the samples suspected of containing the antigen are immobilized onto the well surface and/or then contacted with the anti-IL-32 message and/or anti-IL-32 translated product antibodies of the invention. After binding and/or washing to remove non-specifically bound immune complexes, the bound anti-IL-32 message and/or anti-IL-32 translated product antibodies are detected. Where the initial anti-IL-32 message and/or anti-IL-32 translated product antibodies are linked to a detectable label, the immune complexes may be detected directly. Again, the immune complexes may be detected using a second antibody that has binding affinity for the first anti-IL-32 message and/or anti-IL-32 translated product antibody, with the second antibody being linked to a detectable label.

Another ELISA in which the antigens are immobilized, involves the use of antibody competition in the detection. In this ELISA, labeled antibodies against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-amino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

B. Immunohistochemistry

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

IV. Pharmaceutical Preparations

Pharmaceutical compositions of the present invention comprise an effective amount of one or more anti-IL-32 monoclonal antibody or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one anti-IL-32 monoclonal antibody or additional active ingredient will be known to those of skill in the art in light of the present disclosure, as exemplified by Remington's Pharmaceutical Sciences, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 1990, incorporated herein by reference). Except insofar as any conventional carrier is incompatible with the active ingredient, its use in the pharmaceutical compositions is contemplated.

The anti-IL-32 monoclonal antibody may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington: The Science and Practice of Pharmacy, $20^{th}$ Ed., incorporated herein by reference).

V. Kits

The present invention also provides various kits comprising an anti-IL-32 monoclonal antibody in a container means. For example, a monoclonal antibody of the present invention may comprise part of an ELISA kit. In certain embodiments, the present invention provides kits which allow for immunologic quantification of IL-32 levels from a biological sample, such as a sample of human blood drawn from a patient who has or is suspected of having a disease (e.g., an inflammatory disease).

The kits may comprise a suitably aliquoted monoclonal anti-IL-32 antibody, lipid and/or additional agent. Compositions of the present invention, whether labeled or unlabeled, as may be used to prepare a standard curve for a detection assay. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the monoclonal anti-IL-32 antibody, lipid, additional agent, and any other reagent containers in close confinement for commercial sale. Such containers may include injection or blow-molded plastic containers into which the desired vials are retained.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation of Recombinant Protein His-IL-32αβγ Expression Vector and Purification of Recombinant Protein His-IL-32αβγ

Human lung carcinoma cell lines A549 transfected by IL-18Rβ chain were treated with IL-18. An mRNA was isolated from A549 cell lines and then isolated mRNA was converted to cDNA by using reverse transcriptase. The cDNA was obtained using PCR (polymerase chain reaction) with IL-32α, β, γ gene specific primers. PCR products were ligated into pPROEX™ HTa (Life Technologies Inc., Gaithersburg, Md., USA) using EcoRI and XbaI restriction enzymes. The pPROEX™ HTa expression vectors were engineered so that the protein being expressed was fused to 6 histidine residues. The recombinant vectors were transformed into E. coli DH5α competent cells (Pharmacia, Les Ulis, France). The transformed DH5α were cultured with shaking in LB media with 100 μg/Ml of ampicillin at 37° C. When the O.D. (optical density) at 600 nm reached 0.4 to 0.6, 1 mM IPTG (Isopropylthio-β-D-galactoside) was added to the culture media for induction. The induced DH5α were cultured overnight at 18° C. The cultured cells were harvested by centrifugation at 6000 rpm for 20 minutes at 4° C. and then resuspended in cell lysis solution (20 mM Tris pH8.0, 50 mM Sodium Phosphate pH 8.0, 300 mM NaCl, 10 mM Imidazole, 5 μg/Ml aprotinin, 100 μM PMSF). The cells were lysed by sonication and then centrifugated at 12000 rpm for 30 minutes at 4° C. Recombinant His-IL-32α, β, γ proteins in supernatant were bound to TALON metal affinity resins (BD Bioscience), washed three times with cell lysis solution to reduce nonspecific binding and then eluted using elution solution (50 mM Tris pH8.0, 50 mM Sodium Phosphate pH 8.0, 300 mM NaCl, 120 mM Imidazole). His-IL-32α, β, γ proteins were resolved by 12% SDS-PAGE (sodium dodecyl sulfate polyacrylamide gel electrophoresis) and identified by Coomasie blue staining and Western blot using anti-His antibodies (FIG. 1).

Example 2

Preparation of Recombinant Protein GST-IL-32αβγ Expression Vector and Purification of Recombinant Protein GST-IL-32αβγ

Figure 2:
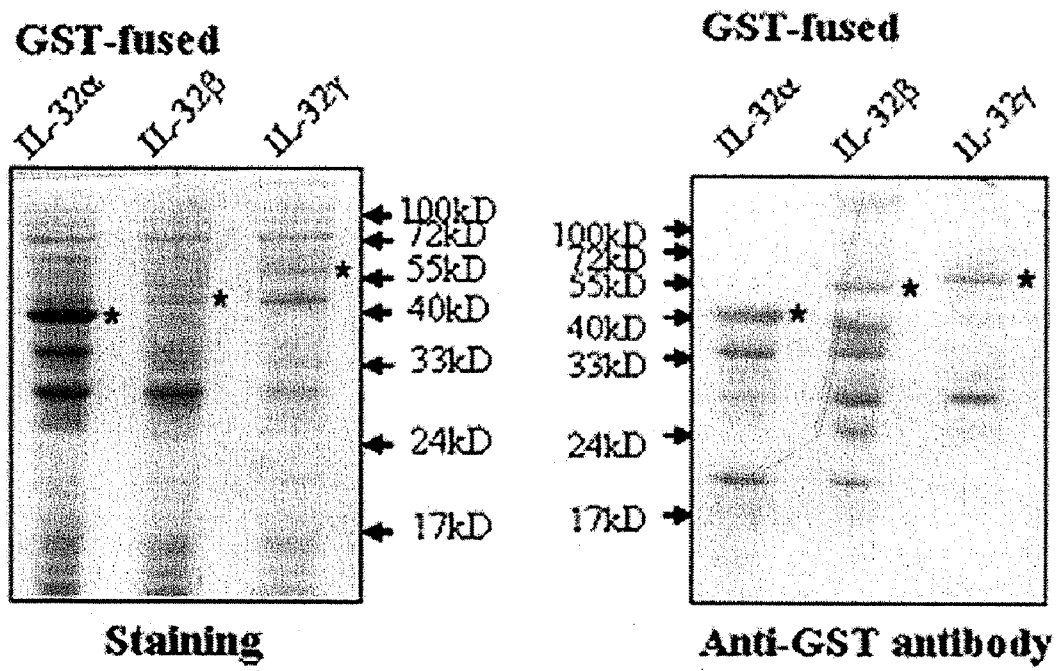
FIG. 2: 12% SDS-PAGE and Western blotting of GST-IL-32α, β, γ recombinant proteins.

GST-fused IL-32 recombinant proteins were made for efficient selection of anti-IL-32 monoclonal antibodies and for optimization of ELISA using anti-IL-32 antibodies. IL-32α, β, γ cDNA and pGEX4T-1(Pharmacia) were cut with EcoRI and XhoI restriction enzymes and then sealed with ligase for 5 hours at 16° C. The IL-32α, β, γ recombinant vectors were transformed into E. coli DH5α competent cells, respectively. The transformed DH5α were cultured with shaking in LB media with 100 μg/Ml of ampicillin at 37° C. When the O.D. at 600 nm reached 0.4 to 0.6, 1 mM IPTG (Isopropylthio-β-D-galactoside) was added to culture media for induction. The induced DH5α were cultured overnight at 18° C. The cultured cells were harvested by centrifugation at 6000 rpm for 20 minutes at 4° C. and then resuspended in cell lysis solution (0.5% Triton X-100, PBS, 5 μg/Ml aprotinin, 100 μM PMSF). The cells were lysed by sonication and then centrifugated at 12000 rpm for 30 minutes at 4° C. Recombinant His-IL-32α, β, γ proteins in supernatant were bound to Glutathion sepharose 4B (Amersham Pharmacia) affinity beads, washed three times with cell lysis solution to reduce nonspecific binding and then eluted using elution solution (50 mM Tris-HCl pH8.0, 20 mM GSH, 5 μg/ml aprotinin, 100 μM PMSF). His-IL-32α, β, γ proteins were resolved by 12% SDS-PAGE and identified by Coomasic blue staining and Western blot using anti-GST antibodies (FIG. 2).

Example 3

Immunization of Mice

A 6-week-old Balb/c mouse was injected intra-peritoneally with 50 μg/100 μl of IL-32α, β, γ, recombinant proteins emulsified in adjuvant, respectively. On day 28, the same amounts of antigen emulsified in adjuvant were injected intra-peritoneally. After 3 or 4 weeks, antibody titer was determined by ELISA. Three days before cell fusion, IL-32α, β, γ recombinant proteins were injected intra-peritoneally without adjuvant.

Example 4

Cell Fusion

After immunized mice were sacrificed, the spleen was aseptically removed and then homogenized. The homogenized cells were suspended in RPMI-1640 cell culture media, treated with erythrocyte lysis solution and then washed sufficiently with RPMI-1640 media. NS-1 myeloma cell line were cultured in RPMI-1640 media containing 10% FBS (fetal bovine serum) before 2 weeks of cell fusion. Splenocyte and NS-1 myeloma cells were mixed in 7-10:1 ratios and then centrifuged. The pellet in the centrifuge tube was dispersed by finger tapping. While lukewarm polyethylene glycol 1 Ml was slowly added over 1 minute, the tube was shaken softly. The fused cells were washed twice with RPMI-1640 media and then resuspended in hybridoma selection RPMI media containing HAT (hypoxanthine aminopterin thymidine) and 10% FBS. Each of 200 μl of the resuspended cells was aliquoted in 96-well microtiter plate, then cultured in a 37° C. $CO_2$ incubator.

Example 5

Screening of Hybridoma

After 2 weeks of culture, fused cells secreting specific antibodies against IL-32α, β, γ proteins, respectively, were screened. Purified GST-fused IL-32α, β, γ recombinant proteins were used as antigens to screen fused cells which secrete antibodies against IL-32α, β, γ, respectively. In order to exclude hybridomas which secret His-specific antibodies, GST-fused IL-32α, β, γ recombinant proteins were used as antigens. (Production of GST-fused IL-32α, β, γ recombinant proteins was performed in similar method to His-fused IL-32 proteins. As previously described in Example 2, pGEX4T-1 was used as an expression vector.) GST-fused IL-32α, β, γ recombinant proteins were coated on a microtiter plate using

Example 6

Manufacture of Primer for Characterization of Selected IL-32 Antibodies

For characterization of IL-32 specific antibodies, primers for deletion mutants of recombinant IL-32α, β, γ were manufactured.

TABLE 1

IL-32 Primers.

| Gene Name | Primers | SEQ ID NOS: |
|---|---|---|
| pGEX4T-1/IL-32α | 5'-CTAGAATTCATGTGCTTCCCGAAG-3'/5'-GCGCTCGAGTCATTTTGAGGATTG-3' | 1 and 2 |
| pGEX4T-1/IL-32β | 5'-CTAGAATTCATGTGCTTCCCGAAG-3'/5'-GCGCTCGAGTCATTTTGAGGATTG-3' | 1 and 2 |
| pGEX4T-1/IL-32γ | 5'-CTAGAATTCATGTGCTTCCCGAAG-3'/5'-GCGCTCGAGTCATTTTGAGGATTG-3' | 1 and 2 |
| pGEX4T-1/IL-32 m1 | 5'-CTAGAATTCATGTGCTTCCCGAAG-3'/5'-CCGCTCGAGTCATGAAGAGAGGCA-3' | 3 and 4 |
| pGEX4T-1/IL-32 m2 | 5'-CTAGAATTCATGTGCTTCCCGAAG-3'/5'-CCGCTCGAGTCACTCCTCATAATA-3' | 5 and 6 |
| pGEX4T-1/IL-32 m3 | 5'-CTAGAATTCATGTGCTTCCCGAAG-3'/5'-CCGCTCGAGTCACTCCTCATAATA-3' | 7 and 8 |
| pGEX4T-1/IL-32 m4 | 5'-CTAGAATTCATGTGCTTCCCGAAG-3'/5'-CCGCTCGAGTCACTTGTCACAAAA-3' | 9 and 10 |
| pGEX4T-1/IL-32 m5 | 5'-CTAGAATTCATGTGCTTCCCGAAG-3'/5'-CCGCTCGAGTCACTTGTCACAAAA-3' | 11 and 12 |
| pGEX4T-1/IL-32 m6 | 5'-GTTGAATTCGTCATGAGATGG-3'/5'-GCGCTCGAGTCATTTTGAGGATTG-3' | 13 and 14 |
| pGEX4T-1/IL-32 m7 | 5'-GTTGAATTCGTCATGAGATGG-3'/5'-ATTCTCGAGCTGGAAAGAGGA-3' | 15 and 16 |
| pGEX4T-1/IL-32 m8 | 5'-ATTGAATTCCACCAGGCCATA-3'/5'-CCGCTCGAGTCACTTGTCACAAAA-3' | 17 and 18 |
| pGEX4T-1/IL-32 m9 | 5'-CCGGAATTCTATTATGAGGAGCAG-3'/5'-GCGCTCGAGTCATTTTGAGGATTG-3' | 19 and 20 |

Figure 3:
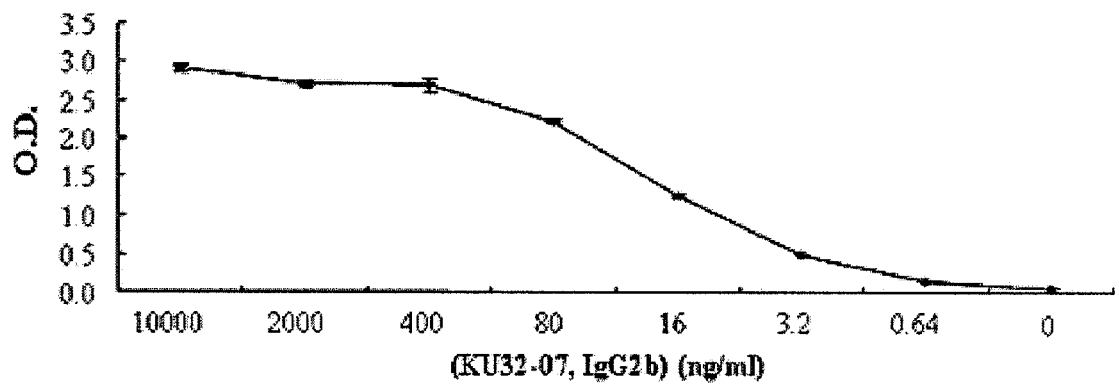
FIG. 3: Graphical representation of monoclonal antibody titer of KU32-07 measured by ELISA.

100 μl (1 μg/Ml) per well and then 100 μl of supernatant of hybridoma culture was added to each well. After 1 hour of reaction at room temperature, microtiter plates were washed three times with phosphate-buffered saline containing Tween-20, horseradish peroxidase-conjugated goat anti-mouse IgGs were then added to plates and then incubated for 1 hour at room temperature. After the plates were washed as above, TMB peroxidase substrate was added and 2.5N sulfuric acid was added to each well to stop the enzyme reaction. Enzyme activity was detected at 450 nm using an ELISA reader. The above data were used to select the hybridomas that secret high affinity antibodies against IL-32 recombinant proteins. By repeating the above steps several times, the hybridoma groups which had the highest affinity could be selected. By limiting dilution, a hybridoma which proliferates from one cell and secrets monoclonal antibodies was selected. The selected clones were designated KU32-07 and KU32-52 and deposited at the Korean Cell Line Research Foundation. The deposit numbers of KU32-07 and KU32-52 were KCLRF-BP-00149 and KCLRF-BP-00150, respectively. Antibody titer of KU32-07 was measured by ELISA. Serially diluted KU32-07 antibodies were added to microliters coated with 1 μg/Ml of IL-32α. After 1 hour of reaction, the horseradish peroxidase-conjugated goat anti mouse IgG and TMB were used for optical density measurement. The result is shown in FIG. 3.

The immunoglobulin class of monoclonal antibodies was determined with an Immuno-Type™ mouse monoclonal antibody isotyping kit. Isotype of monoclonal antibody secreted by KU32-07 was IgG2b, and that of KU32-52 was IgG1.

Example 7

Characterization of Antibodies Specific for IL-32

Figure 4:
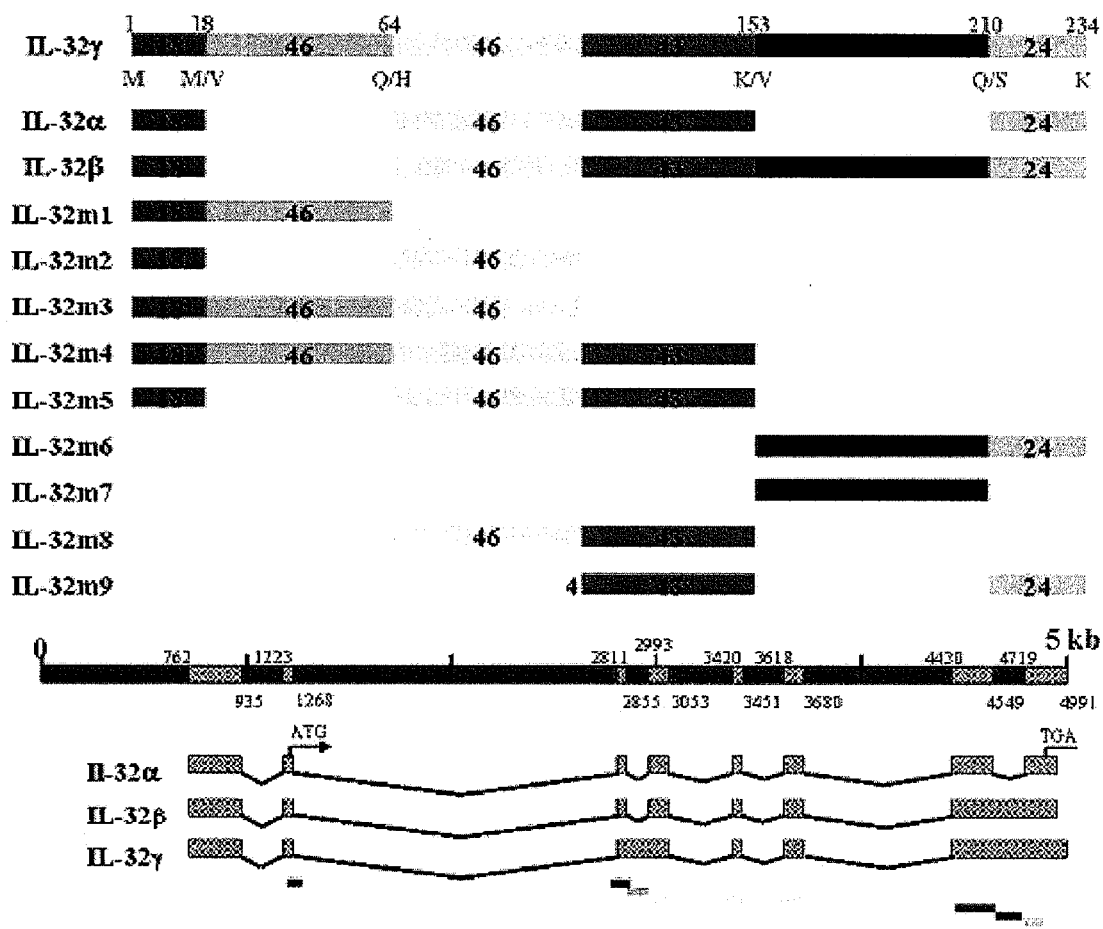
FIG. 4: A schematic diagram of deletion mutant gene of IL-32.
Figure 5:
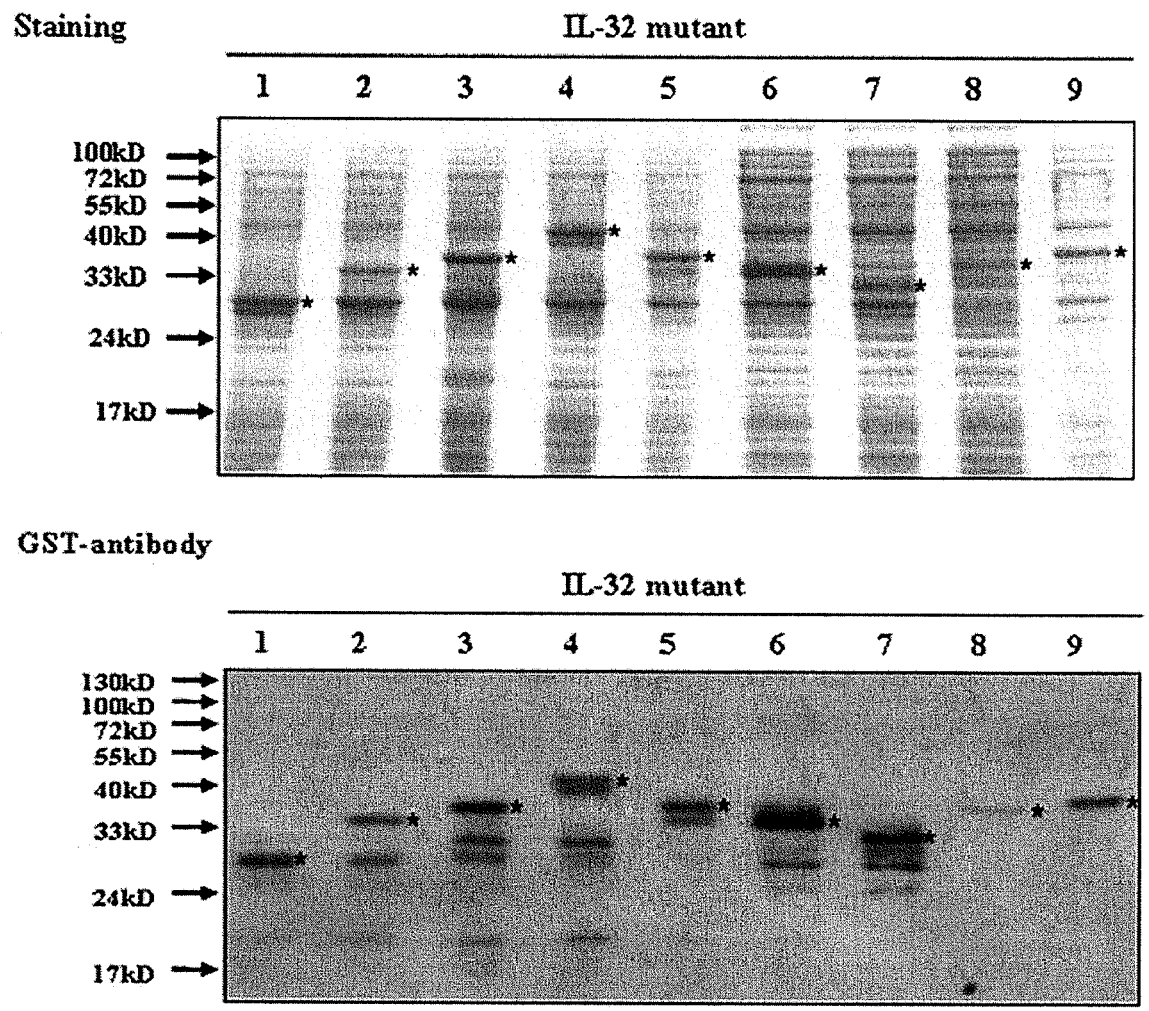
FIG. 5: 12% SDS-PAGE and Western blotting of deletion mutant of IL-32 protein.
Figure 6:
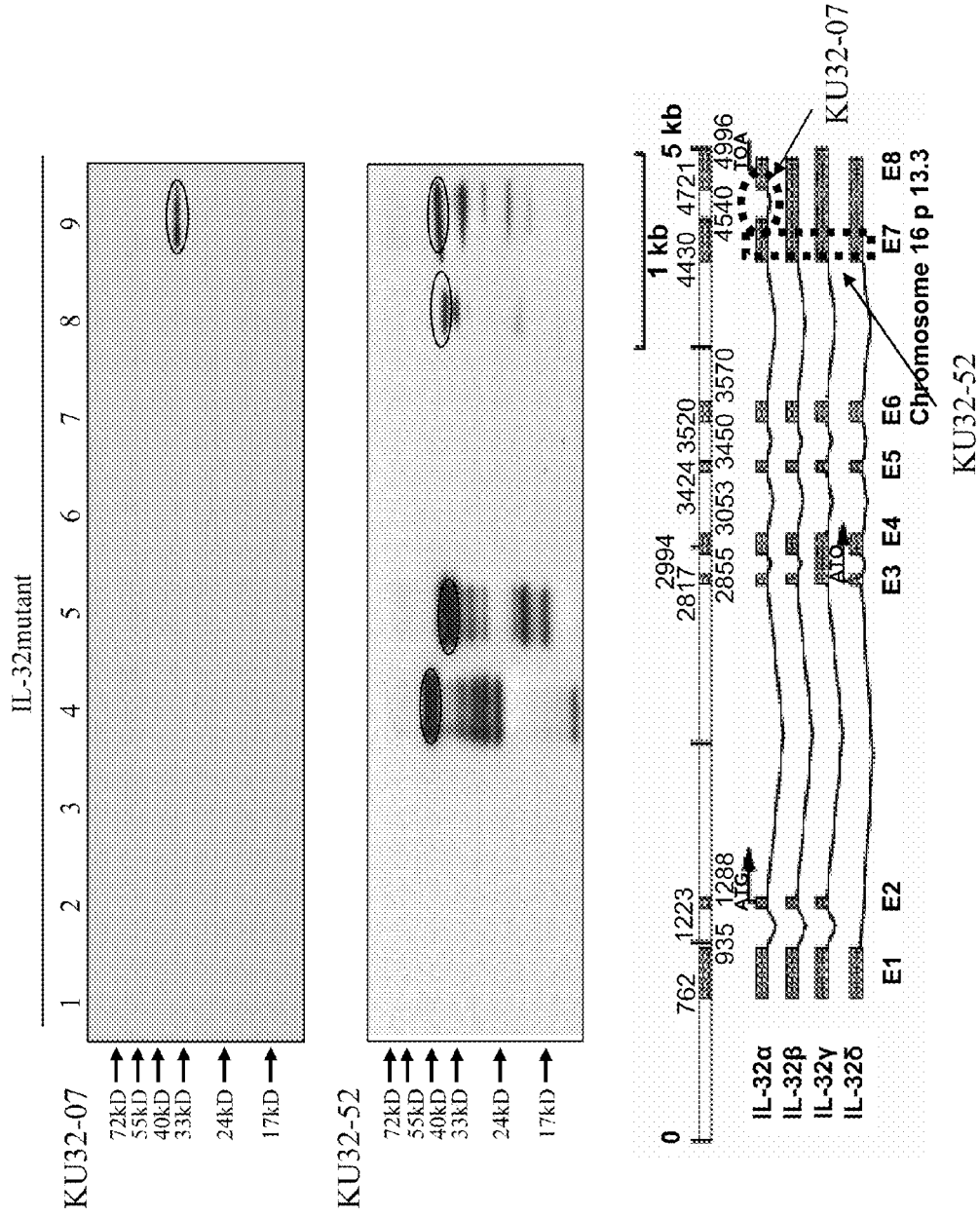
FIG. 6: Western blotting using KU32-07 monoclonal antibody and KU32-52 monoclonal antibody for detection of IL-32 m1 to IL-32 m9.
Figure 7:
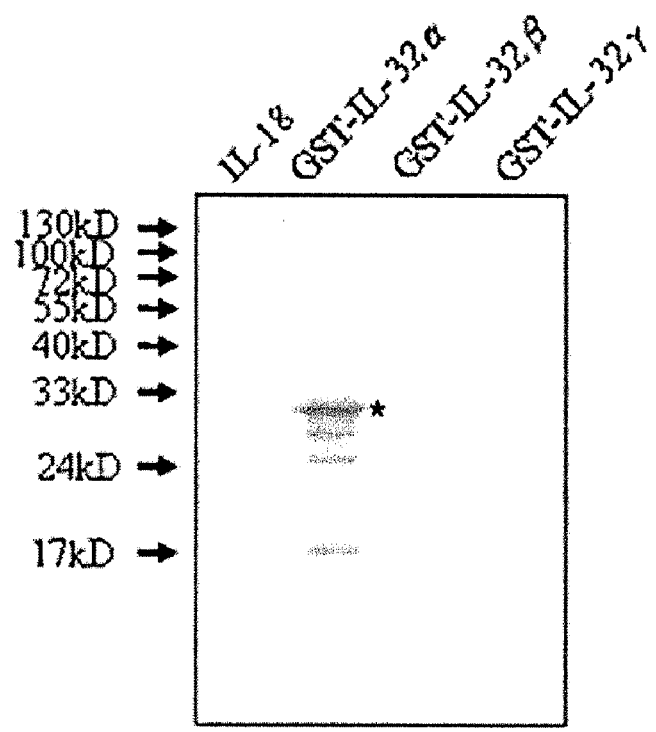
FIG. 7: Western blotting using KU32-07 monoclonal antibody and KU32-52 monoclonal antibody for detection of IL-32α, β, γ proteins.
Figure 7:
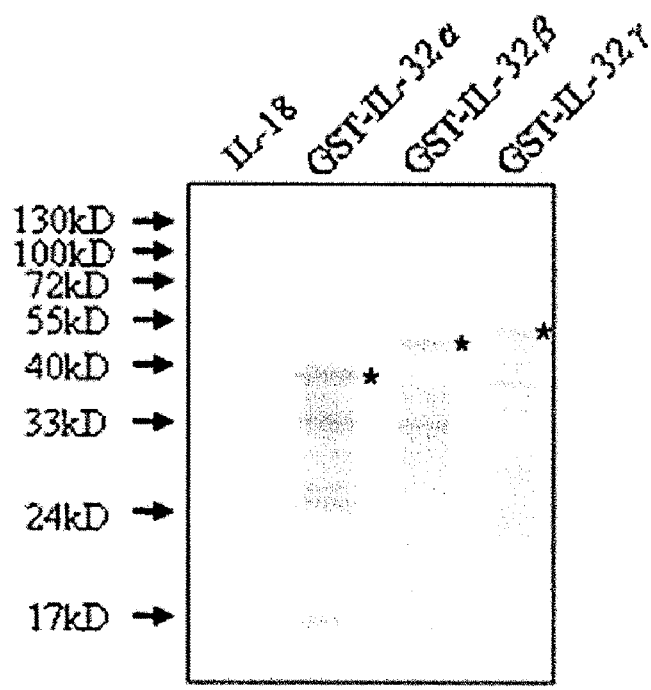
Figure 8:
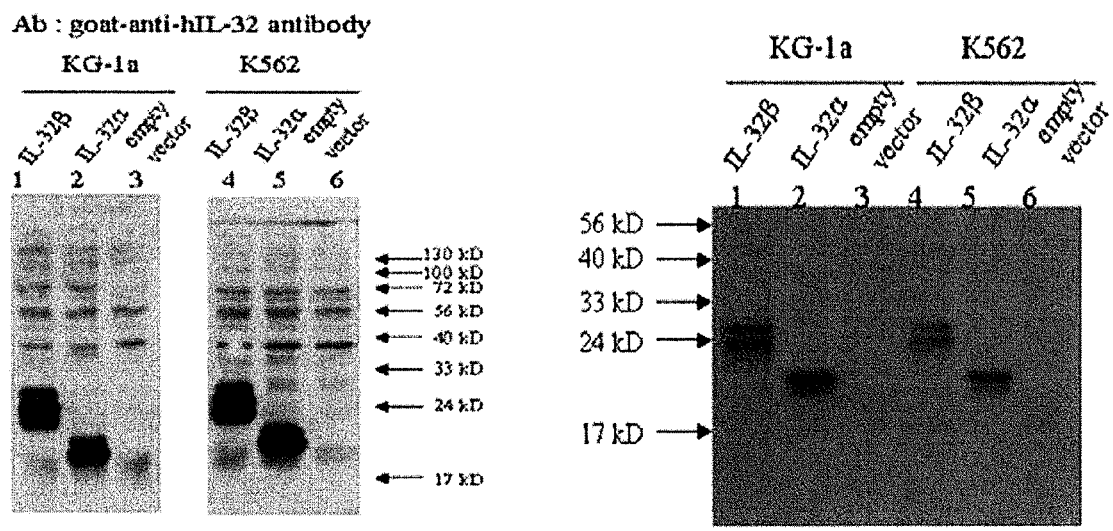
FIG. 8: Western blotting using goat anti-hIL-32 polyclonal antibody and KU32-52 monoclonal antibody for detection of IL-32 expressed by IL-32 over-expression cell lines.
Figure 9:
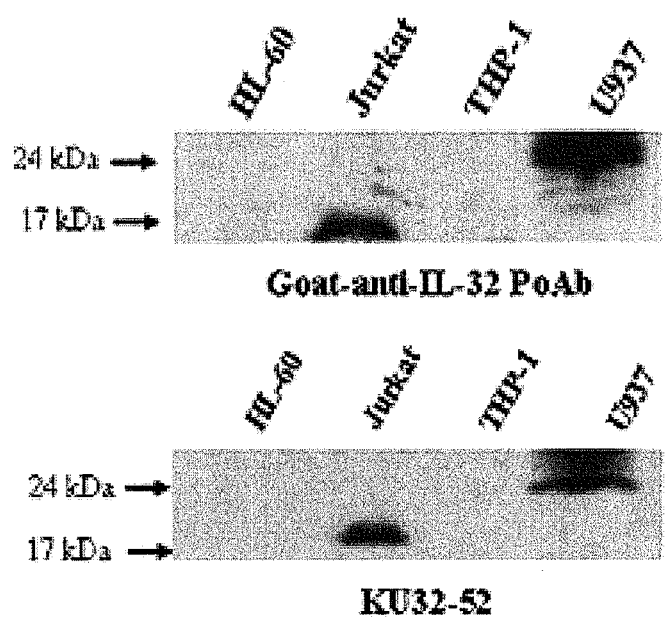
FIG. 9: Western blotting using goat anti-hIL-32 polyclonal antibody and KU32-52 monoclonal antibody for detection of IL-32 expressed by various immune cell lines.

In order to characterize antibodies specific for IL-32, various deletion mutants of recombinant IL-32α, β, γ were made (FIG. 4). Cloning of deletion mutants of recombinant IL-32α, β, γ was performed using the same method described in Example 1, and pGEX4T-1 was used as a cloning vector. GST-fused mutant proteins were expressed in E. coli and then purified. Purified GST-fused mutant proteins were resolved by 12% SDS-PAGE and identified by Coomassie blue staining and Western blot using anti-GST antibodies (FIG. 5). For epitope mapping, GST-fused mutant proteins were resolved in 12% SDS-PAGE and transferred into a polyvinylidenedisulfide (PVDF) membrane. The membrane was blocked with 5% skimmed milk for 2 hours and then incubated with supernatant of hybridoma culture at room temperature for 1 hour. After washing with PBS containing Tween-20, the membrane was reacted with peroxidase-conjugated anti-mouse IgG at room temperature for 1 hour, washed and treated with enhanced chemiluminescence (ECL) solution. As the result of western blotting (FIG. 6), it was suggested that KU32-07 antibody (antibody secreted by hybridoma KU32-07 was designated KU32-07 antibody for your convenience, the same as KU32-52 antibody) recognized the protein region that was expressed from 4549~4991 bp region of the IL-32αgene (from amino acids 91 to 131 of IL-32α), KU32-52 antibody recognized the protein region that was expressed from 4430~4549 bp region of the IL-32 gene (from amino acids 71 to 107 of IL-32β). So, it could be concluded that KU32-07 antibody recognized only IL-32α, but KU32-52 antibody recognized IL-32α, β, γ altogether. For the confirmation of above result, Western blot using GST-fused IL-32α, β, γ was performed. It was observed that KU32-07 antibody recognized only IL-32α, whereas the KU32-52 antibody recognized IL-32α, β, γ (FIG. 7). In order to confirm whether the KU32-52 antibody could detect intact IL-32 in mammalian cells, cell lines expressing IL-32 cc or IL-32β were made by transfection. Expression of IL-32α or IL-32β was confirmed by Western blotting. FIG. 8 shows that the KU32-52 monoclonal antibody recognized IL-32 expressed in IL-32 overexpression cell lines. FIG. 9 shows that the KU32-52 monoclonal antibody also recognized IL-32 expressed in various immune cell lines.

Example 8

Production of Ascites and Purification of Antibodies

Hybridoma KU32-07 and KU32-52 clones ($5 \times 10^6$ cells) were intra-peritoneally injected into an Balb/c mouse pre-injected with 100 μl of Freund's incomplete adjuvant, respectively. After a week, the ascites were removed with an 18 G sterile needle and supernatants were collected by centrifugation. Antibodies were purified using Protein A/G Sepharose (Bio-Rad), and eluted with glycine-HCl (pH2.7). Purified antibodies were dialyzed with PBS, concentrated, and stored at −70° C.

Example 9

Optimization of Sandwich ELISA System Using Monoclonal Antibodies Specific for IL-32

Figure 10:
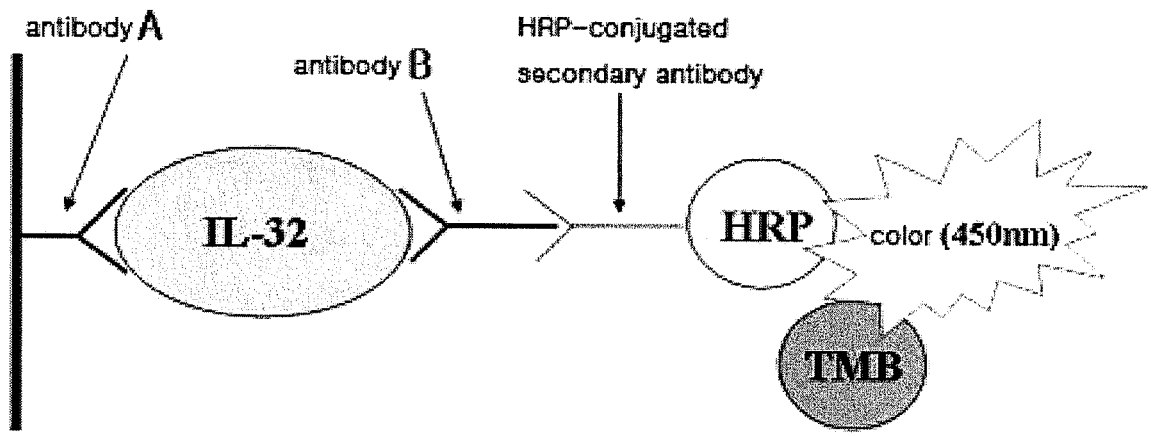
FIG. 10: A diagram of a sandwich ELISA for quantification of IL-32α.
Figure 11:
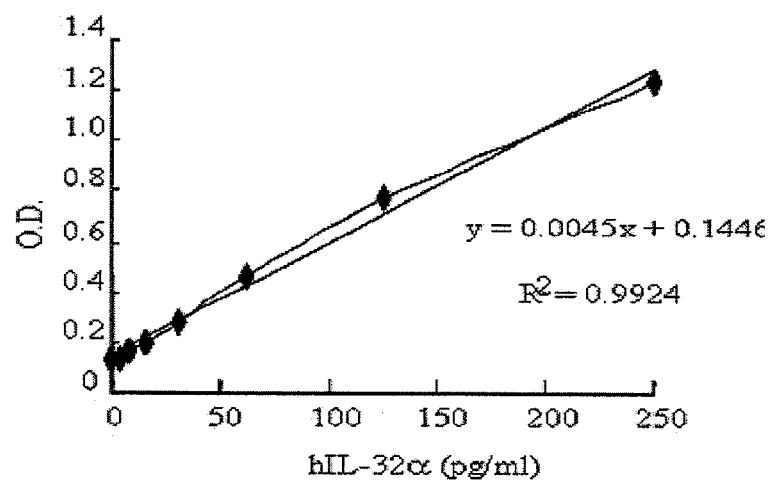
FIG. 11: A graphical representation of sandwich ELISA using the KU32-07 monoclonal antibody for detection of IL-32α.

A sandwich ELISA was designed for easy quantification of IL-32α in human blood (FIG. 10). The microtiter plate wells were coated with 100 μl (1 μg/Ml) of IL-32 polyclonal antibody and then sufficiently washed. The plate was blocked with 1% BSA (bovine serum albumin) for 2 hours and then washed. Serially diluted IL-32α, β, γ(100 μl/well) were added to the plate and reacted at room temperature for 1 hour. The plate was washed with PBS containing Tween-20 three times and then reacted with 1 μg/Ml of KU32-07 monoclonal antibody for 1 hour. After the plate was washed, the horseradish peroxidase-conjugated goat anti-mouse IgG were added to the plate and then incubated for 1 hour at room temperature. After the plate was sufficiently washed, TMB peroxidase substrate was added and the enzyme activity was detected at 450 nm. ELISA data indicated that the KU32-07 monoclonal antibody specifically recognized IL-32αproteins and effectively detected the concentration of IL-32α (FIG. 11).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,938,948
U.S. Pat. No. 5,021,236
U.S. Pat. No. 5,196,066
Abbondanzo et al., *Breast Cancer Res. Treat.*, 16:182(151), 1990.
Allred et al., *Breast Cancer Res. Treat.*, 16:182(149), 1990.
Antibodies: A Laboratory Manual, Cold Spring Harbor Laboratory, 1988
Asquith and McInnes, *Curr. Opin. Rheumatol.*, 19(3):246-251, 2007.
Atherton et al., *Biol. of Reproduction*, 32:155-171, 1985.
Berberian et al., *Science*, 261:1588-1591, 1993.
Breenan and Beech, *Curr. Opin. Rheumatol.*, 19(3):296-301, 2007.
Brown et al., *Immunol Ser,* 53:69-82, 1990.
Campbell, In: *Monoclonal Antibody Technology, Laboratory Techniques in Biochemistry and Molecular Biology*, Burden and Von Knippenberg (Eds.), Elseview, Amsterdam, 75-83, 1984.
Cleary et al., *Trends Microbiol.*, 4:131-136, 1994.
Conti et al., *Autoimmun. Rev.*, 6(3):131-137, 2007.
De Jager et al., *Semin. Nucl. Med.*, 23(2):165-179, 1993.
Dholakia et al., *J. Biol. Chem.*, 264, 20638-20642, 1989.
Dinarello and Kim, *Ann. Rheum. Dis.*, 65(3):iii61-64, 2006.
Doolittle and Ben-Zeev, *Methods Mol. Biol.*, 109:215-237, 1999.
Gefter et al., *Somatic Cell Genet.*, 3:231-236, 1977.
Goda et al., *Int. Immunol.*, 18(2):233-240, 2006.
Goding, In: *Monoclonal Antibodies: Principles and Practice*, 2d ed., Academic Press, Orlando, Fla., pp 60-61, 65-66, 71-74, 1986.
Gulbis and Galand *Hum. Pathol.*, 24(12):1271-1285, 1993.
Joosten et al., *Proc. Natl. Acad. Sci. USA,* 103(9):3298-3303, 2006.
Kang et al., *Science,* 240:1034-1036, 1988.
Khatoon et al., *Ann. of Neurology*, 26:210-219, 1989.
Kim et al. *Immunity,* 22(1):131-142, 2005.
King et al., *J. Biol. Chem.*, 269:10210-10218, 1989.
Kohler and Milstein, *Eur. J. Immunol.*, 6:511-519, 1976.
Kohler and Milstein, *Nature,* 256:495-497, 1975.
Kohler et al., *Methods Enzymol.*, 178:3, 1989.
Kreier et al., In: *Infection, Resistance and Immunity*, Harper & Row, NY, 1991.
Kundu and Basu, *PLoS Med.,* 3(8):e274, 2006.
Lenert et al., *Science,* 248:1639-1643, 1990.
Nakamura et al., In: *Handbook of Experimental Immunology* (4th Ed.), Weir et al. (Eds), 1:27, Blackwell Scientific Publ., Oxford, 1987.
Netea et al., *PLoS Med.,* 3(8):e277, 2006.
O'Shannessy et al., *J. Immun. Meth.*, 99:153-161, 1987.
Owens & Haley, *J. Biol. Chem.,* 259:14843-14848, 1987.
Potter & Haley, *Meth. in Enzymol.,* 91, 613-633, 1983.

Remington's Pharmaceutical Sciences, 18th Ed. Mack Printing Company, pp. 1289-1329, 1990.

Remington's Pharmaceutical Sciences, 20th Ed. Lippincott Williams & Wilkins, 2003.

Sasso et al., *J. Immunol.*, 142:2778-2783, 1989.

Shorki et al., *J. Immunol.*, 146:936-940, 1991.

Silvermann et al., *J. Clin. Invest.*, 96:417-426, 1995.

What is claimed is:

1. A monoclonal antibody which selectively binds an interleukin-32 (IL-32) protein, wherein the antibody is the KU32-07 or KU32-52 antibody.

2. The monoclonal antibody of claim 1, wherein the antibody is the KU32-07 antibody.

3. The monoclonal antibody of claim 1, wherein the antibody is the KU32-52 antibody.

4. The monoclonal antibody of claim 1, wherein said antibody is labeled with a magnetic spin resonance label, a fluorescent label, a radiolabel, a chemiluminescent label, a fluorochrome, or an enzyme.

5. The monoclonal antibody of claim 1, wherein said monoclonal antibody is conjugated with a radioisotope, a chemotherapeutic, a toxin, a cytokine or an enzyme.

6. The monoclonal antibody of claim 1, wherein the antibody is comprised in a pharmaceutical preparation.

7. A hybridoma cell producing a monoclonal antibody of claim 1.

8. The hybridoma cell of claim 7, wherein the hybridoma cell is KCLRF-BP-00149.

9. The hybridoma cell of claim 7, wherein the hybridoma cell is KCLRF-BP-00150.

10. A kit comprising the monoclonal antibody of claim 1 in a suitable container.

11. The kit of claim 10, wherein the kit further comprises a polyclonal antibody specific for said IL-32 protein in a second container.

12. The kit of claim 10, wherein the kit further comprises reagents for an ELISA test for measuring the presence, absence, or amount of said IL-32 protein.

13. The kit of claim 10, wherein the kit comprises a monoclonal antibody which selectively recognizes IL-32α.

14. The kit of claim 10, wherein the monoclonal antibody is KU32-07.

15. The kit of claim 10, wherein the kit further comprises reagents for a radioimmunoassay (RIA), immunoradiometric assay, fluoroimmunoassay, chemiluminescent assay, bioluminescent assay, or Western blot for measuring the presence, absence, or amount of said IL-32 protein.

* * * * *

SEQUENCE LISTING

<160> NUMBER OF SEQ ID NOS: 20

<210> SEQ ID NO 1
<211> LENGTH: 24
<212> TYPE: DNA
<213> ORGANISM: artificial sequence
<220> FEATURE:
<223> OTHER INFORMATION: forward primer for the amplification of IL-32 gene

<400> SEQUENCE: 1
ctagaattca tgtgcttccc gaag                                          24

<210> SEQ ID NO 2
<211> LENGTH: 24
<212> TYPE: DNA
<213> ORGANISM: artificial sequence
<220> FEATURE:
<223> OTHER INFORMATION: backward primer for the amplification of IL-32 gene

<400> SEQUENCE: 2
gcgctcgagt cattttgagg attg                                          24

<210> SEQ ID NO 3
<211> LENGTH: 24
<212> TYPE: DNA
<213> ORGANISM: artificial sequence
<220> FEATURE:
<223> OTHER INFORMATION: forward primer for the amplification of IL-32m1 deletion mutant

<400> SEQUENCE: 3
ctagaattca tgtgcttccc gaag                                          24

<210> SEQ ID NO 4
<211> LENGTH: 24
<212> TYPE: DNA
<213> ORGANISM: artificial sequence
<220> FEATURE:
<223> OTHER INFORMATION: backward primer for the amplification of IL-32m1 deletion mutant

<400> SEQUENCE: 4
ccgctcgagt catgaagaga ggca                                          24

<210> SEQ ID NO 5
<211> LENGTH: 24
<212> TYPE: DNA
<213> ORGANISM: artificial sequence
<220> FEATURE:
<223> OTHER INFORMATION: forward primer for the amplification of IL-32m2 deletion mutant

<400> SEQUENCE: 5
ctagaattca tgtgcttccc gaag                                          24

<210> SEQ ID NO 6
<211> LENGTH: 24
<212> TYPE: DNA

-continued

<213> ORGANISM: artificial sequence
<220> FEATURE:
<223> OTHER INFORMATION: backward primer for the amplification of
      IL-32m2 deletion mutant

<400> SEQUENCE: 6
ccgctcgagt cactcctcat aata                                          24

<210> SEQ ID NO 7
<211> LENGTH: 24
<212> TYPE: DNA
<213> ORGANISM: artificial sequence
<220> FEATURE:
<223> OTHER INFORMATION: forward primer for the amplification of IL-32m3
      deletion mutant

<400> SEQUENCE: 7
ctagaattca tgtgcttccc gaag                                          24

<210> SEQ ID NO 8
<211> LENGTH: 24
<212> TYPE: DNA
<213> ORGANISM: artificial seqence
<220> FEATURE:
<223> OTHER INFORMATION: backward primer for the amplification of
      IL-32m3 deletion mutant

<400> SEQUENCE: 8
ccgctcgagt cactcctcat aata                                          24

<210> SEQ ID NO 9
<211> LENGTH: 24
<212> TYPE: DNA
<213> ORGANISM: artificial sequence
<220> FEATURE:
<223> OTHER INFORMATION: forward primer for the amplification of IL-32m4
      deletion mutant

<400> SEQUENCE: 9
ctagaattca tgtgcttccc gaag                                          24

<210> SEQ ID NO 10
<211> LENGTH: 24
<212> TYPE: DNA
<213> ORGANISM: artificial sequence
<220> FEATURE:
<223> OTHER INFORMATION: backward primer for the amplification of
      IL-32m4 deletion mutant

<400> SEQUENCE: 10
ccgctcgagt cacttgtcac aaaa                                          24

<210> SEQ ID NO 11
<211> LENGTH: 24
<212> TYPE: DNA
<213> ORGANISM: artificial sequence
<220> FEATURE:
<223> OTHER INFORMATION: forward primer for the amplification of
      IL-32m5 deletion mutant

<400> SEQUENCE: 11
ctagaattca tgtgcttccc gaag                                          24

<210> SEQ ID NO 12
<211> LENGTH: 24
<212> TYPE: DNA
<213> ORGANISM: artificial sequence

```
<220> FEATURE:
<223> OTHER INFORMATION: backward primer for the amplification of
      IL-32m5 deletion mutant

<400> SEQUENCE: 12
ccgctcgagt cacttgtcac aaaa                                          24

<210> SEQ ID NO 13
<211> LENGTH: 21
<212> TYPE: DNA
<213> ORGANISM: artificial sequence
<220> FEATURE:
<223> OTHER INFORMATION: forward primer for the amplification of
      IL-32m6 deletion mutant

<400> SEQUENCE: 13
gttgaattcg tcatgagatg g                                             21

<210> SEQ ID NO 14
<211> LENGTH: 24
<212> TYPE: DNA
<213> ORGANISM: artificial sequence
<220> FEATURE:
<223> OTHER INFORMATION: backward primer for the amplification of
      IL-32m6 deletion mutant

<400> SEQUENCE: 14
gcgctcgagt cattttgagg attg                                          24

<210> SEQ ID NO 15
<211> LENGTH: 21
<212> TYPE: DNA
<213> ORGANISM: artificial sequence
<220> FEATURE:
<223> OTHER INFORMATION: forward primer for the amplification of
      IL-32m7 deletion mutant

<400> SEQUENCE: 15
gttgaattcg tcatgagatg g                                             21

<210> SEQ ID NO 16
<211> LENGTH: 21
<212> TYPE: DNA
<213> ORGANISM: artificial sequence
<220> FEATURE:
<223> OTHER INFORMATION: backward primer for the amplification of
      IL-32m7 deletion mutant

<400> SEQUENCE: 16
attctcgagc tggaaagagg a                                             21

<210> SEQ ID NO 17
<211> LENGTH: 21
<212> TYPE: DNA
<213> ORGANISM: artificial sequence
<220> FEATURE:
<223> OTHER INFORMATION: forward primer for the amplification of
      IL-32m8 deletion mutant

<400> SEQUENCE: 17
attgaattcc accaggccat a                                             21

<210> SEQ ID NO 18
<211> LENGTH: 24
<212> TYPE: DNA
<213> ORGANISM: artificial sequence
<220> FEATURE:
```

```
<223> OTHER INFORMATION: backward primer for the amplification of
      IL-32m8 deletion mutant

<400> SEQUENCE: 18
ccgctcgagt cacttgtcac aaaa                                              24

<210> SEQ ID NO 19
<211> LENGTH: 24
<212> TYPE: DNA
<213> ORGANISM: artificial sequence
<220> FEATURE:
<223> OTHER INFORMATION: forward primer for the amplification of
      IL-32m9 deletion mutant

<400> SEQUENCE: 19
ccggaattct attatgagga gcag                                              24

<210> SEQ ID NO 20
<211> LENGTH: 24
<212> TYPE: DNA
<213> ORGANISM: artificial sequence
<220> FEATURE:
<223> OTHER INFORMATION: backward primer for the amplification of
      IL-32m9 deletion mutant

<400> SEQUENCE: 20
gcgctcgagt cattttgagg attg                                              24
```